(12) United States Patent
Sierra et al.

(10) Patent No.: US 7,018,396 B2
(45) Date of Patent: Mar. 28, 2006

(54) METHOD OF TREATING ACNE

(75) Inventors: Rafael A. Sierra, Palmer, MA (US);
Mirko Mirkov, Chelmsford, MA (US);
Kathleen I. McMillan, Concord, MA (US); Jennifer R. Lloyd, Poland, OH (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 09/924,156

(22) Filed: Aug. 7, 2001

(65) Prior Publication Data

US 2003/0050678 A1 Mar. 13, 2003

(Under 37 CFR 1.47)

(51) Int. Cl.
*A61N 5/00* (2006.01)

(52) U.S. Cl. .............................. 607/89; 607/88; 606/3; 606/9; 128/898

(58) Field of Classification Search .................. 607/88, 607/89; 606/3, 9; 128/898
See application file for complete search history.

(56) References Cited

U.S. PATENT DOCUMENTS

| | | | | |
|---|---|---|---|---|
| 5,066,293 A | | 11/1991 | Furumoto | 606/9 |
| 5,257,970 A | | 11/1993 | Dougherty | 604/20 |
| 5,304,170 A | | 4/1994 | Green | 606/9 |
| 5,312,395 A | | 5/1994 | Tan et al. | 606/9 |
| 5,346,488 A | | 9/1994 | Prince et al. | 606/7 |
| 5,749,868 A | | 5/1998 | Furumoto | 606/9 |
| 5,817,089 A | | 10/1998 | Tankovich et al. | 606/9 |
| 6,036,684 A | * | 3/2000 | Tankovich et al. | 606/9 |
| 6,183,773 B1 | * | 2/2001 | Anderson | 424/450 |
| 6,235,016 B1 | * | 5/2001 | Stewart | 606/9 |
| 6,338,855 B1 | * | 1/2002 | Albacarys et al. | 424/409 |
| 6,600,951 B1 | * | 7/2003 | Anderson | 604/20 |

OTHER PUBLICATIONS

Böhm and Luger, "The Pilosebaceous Unit is Part of the Skin Immune System," *Dermatology*, 196:75–79, 1998.

Cunliffe, "Acne Vulgaris. The Past, the Present and the Future," *Acta Bermatovener (Stockh) Suppl. 120*, pp. 34–38, 1985.

Dufresne et al., "Squamous cell carcinoma arising from the follicular occlusion triad," *J. Am. Acad. Dermatol.* 35(3), Part 1:475–477, 1996.

Fallon Friedlander, "Effective Treatment of Acne Fulminans–Associated Granulation Tissue with the Pulsed Dye Laser," *Pediatric Dermatology*, 15(5):396–398, 1998.

Friedman–Birnbaum et al., "Seborrheic Skin and Acne Vulgaris as Protective Factors against the Development of Basal Cell Epithelioma," *Dermatolgica*, 183:160–163, 1991.

Johnsson et al., "No photoinactivation of Propionibacterium acnes with soft laser treatment," *Dermatologica*, 175(1):50, 1987.

Kantor et al., "Treatment of acne keloidalis nuchae with carbon dioxide laser," *J. Am. Acad. Dermatol.*, 14:263–267, 1986.

(Continued)

*Primary Examiner*—A. Farah
(74) *Attorney, Agent, or Firm*—Fish & Richardson P.C.

(57) ABSTRACT

A method of selectively enhancing photothermal sebaceous gland disruption and treatment of acne is disclosed. The method provides for alleviation of the acne symptoms as well as preventing acne recurrence and new acne from occurring.

20 Claims, 5 Drawing Sheets

(3 of 5 Drawing Sheet(s) Filed in Color)

OTHER PUBLICATIONS

Lesnik et al., "Agents that cause enlargement of sebaceous glands in hairless mice," *Arch. Dermatol.*, 284:100–105, 1992.

Lucchina et al., "Fluorescence photography in the evaluation of acne," *J. Am. Acad. Dermatol.* 35:58–63 (1996).

Manuskiatti et al., "Laser hair removal affects sebaceous glands and sebum excretion . . . ," *J. Am. Acad. Dermatol.*, 41:176–180, 1999.

Shuster, "Acne: The Ashes of a Burnt Out Controversy," *Acta Derm. Venereol. Suppl. (Stockh)*, 120:43–46, 1985.

Sigurdsson et al., "Phototherapy of Acne Vulgaris with Visible Light," *Dermatology*, 194:256–260, 1997.

Strauss et al., "Skin Lipids and Acne," *Annu. Rev. Med., 26*: 27–31, 1975.

Sumian et al., "A new method to improve penetration depth of dyes into the follicular duct :. . . ," *J. Am. Acad. Dermotol.*, 41(2) Part 1:172–175, 1999.

* cited by examiner

METHOD OF TREATING ACNE

BACKGROUND OF THE INVENTION

1. Field of the Invention

Embodiments of the present invention relate in general to the combined use of laser therapy and laser light absorbing agents in the treatment of skin conditions associated with the production of sebum by sebaceous glands. More particularly, embodiments of the present invention relate to methods of preventing, reducing, eliminating, or otherwise treating unwanted skin conditions, such as acne, using laser light and one or more exogenous chromophores to disrupt production of sebum without significant harm to surrounding normal tissue.

2. Description of Related Art

Unwanted skin conditions associated with the production or overproduction of sebum are well known. One example of such an unwanted skin condition includes common acne which is a major treatment concern of many dermatologists. It is estimated that as many as 32 million Americans exhibit some form of unwanted acne.

The treatment of acne is of major concern to dermatologists. Acne accounts for more than four million visits to dermatologists each year. Typically, acne arises in the early teen years and subsides by the mid twenties. In many cases, particularly in women, acne remains a chronic problem well into the adult years. It is estimated that as many as 32 million Americans suffer from acne.

Acne vulgaris, the most common form of acne, is the result of the secretion of sebum by the sebaceous gland into a blocked pore. Continued secretion results in buildup of the sebum in the blocked pore. Bacteria in the pore gives rise to infection and a common unsightly skin condition known as pimples. Sebaceous gland hyperplasia is also a common form of acne in which the sebaceous gland grows or become enlarged as a result of overproduction of sebum. A pimple is formed even if the gland is not blocked.

Sebaceous glands and the sebum they produce apparently have no commonly accepted significant function in humans. The skin of young children does not appear to be negatively affected by the almost total lack of sebum. The only known role of sebum in humans is in the pathogenesis of acne. In the past, physicians treated acne with radiation therapy to destroy the sebaceous gland. Radiation, however, does not specifically target the sebaceous glands, and can cause significant morbidity to normal tissue because of its mutagenic toxicity. Increased risk of cutaneous carcinoma has also been associated with radiation therapy. Current acne treatments do not eradicate the sebaceous glands selectively and without harm to surrounding normal tissue, and therefore remain non-curative and inadequate. The result is years of chronic therapy and potential scarring for the patient.

Selective photothermolysis is a method of causing selective and irreversible photothermal damage to tissue structures containing a chromophore that can be used to distinguish that target structure from surrounding tissue. For a light source, typically a laser, to be useful for selective photothermolysis, it must emit with sufficient intensity at a wavelength preferentially absorbed by the target chromophore. The pulse duration or exposure time of the source must be less than the thermal relaxation time of the target to minimize temperature increases in tissue surrounding the target. Techniques based on this concept using well known laser systems are well established for treatment of benign cutaneous vascular lesions such as portwine stain (PWS), birthmarks, telangiectasias, hemangiomas, warts, psoriasis, arthritis in which hemoglobin in the abnormal ectatic lesional vasculature serves as the chromophore and the target is the vessel wall, as well as, atherosclerotic plaque and other desired applications. See U.S. Pat. No. 5,312,395; U.S. Pat. No. 5,749,868; U.S. Pat. No. 5,257,970; U.S. Pat. No. 5,066,293, U.S. Pat. No. 5,346,488, "Selective Photothermolysis: Precise Microsurgery by Selective Absorption of Pulsed Radiation", Anderson et al., Science, 220:524–527 (1983); Spears et al. J. Clin. Invest, 71, 39–399 (1983), the disclosure of each of which is hereby incorporated by reference in their entireties for all purposes. The deepest blood vessels contributing to the color of PWS lesions are approximately 1 mm below the skin surface, and are accessible to selective photothermal targeting using available lasers such as the 585 nm pulsed dye laser. The theoretical advantages of selective photothermolysis have been borne out in clinical studies showing that PDL (pulsed dye laser) treatment of benign cutaneous vascular lesions is associated with very low risk of scarring. However, photothermolysis techniques involving the direction of laser light onto the surface of skin would be more effective if the laser light was not substantially absorbed by components of skin and particularly if an exogenous chromophore was used which selectively collected in the targeted tissue and which absorbed laser light at a wavelength substantially outside that absorbed by normal skin components.

One approach to the treatment of acne is to reduce the production of sebum by disrupting or even destroying the sebaceous gland. One such method described in U.S. Pat. No. 5,817,089 includes forcing, for example by the use of ultrasound, an exogenous chromophore into spaces within or adjacent sebaceous glands. The chromophore is then illuminated with short pulses of laser light so as to provide sufficient energy to the chromophore to create explosions which blow off layers of dead skin cells and/or destroy tissue responsible for hair growth and/or sebum production.

The use of beta-carotene as an exogenous chromophore along with lasers to treat acne is considered in U.S. Pat. No. 5,304,170. However, the laser light has a wavelength between 425 nm and 550 nm which suffers from poor penetration within the tissues. Further, while beta-carotene does collect in sebaceous glands, it also collects in the tissue between the glands and surrounding tissue and skin components, resulting in poor selectivity and yellowing of the skin.

Efforts to use lasers to treat certain skin conditions and to effect hair removal include Manuskiatti et al., J. Am. Acad. Dermatol., vol. 41, Number 2, Part 1, pp. 176–180 (1999), Friedlander, Pediatric Dermatology, vol. 15, No. 5, pp. 396–398 (1998), Shuster, Acta Dermatovener (Stockh) Suppl., 120, pp. 43–46, Sigurdsson et al., Dermatology, 194, pp. 256–260 (1997), Sumian et al., J. Am. Acad. Dermatol., Vol. 41, Number 2, Part 1, pp. 172–175 (1999), the disclosure of each of which is hereby incorporated by reference in their entireties for all purposes. However, these efforts do not recognize the use of laser light having a wavelength outside that significantly absorbed by skin or skin components or the use of an exogenous chromophore which can be selectively introduced to sebaceous glands.

Accordingly, there is a need in the art to provide methods of treating unwanted skin conditions associated with sebum production or overproduction which employ laser light having a wavelength outside that substantially absorbed by skin or skin components. There is also a further need in the art to selectively localize the effects of photothermolysis to sebaceous glands using a chromophore which absorbs laser light having a wavelength outside that substantially absorbed by skin or skin components and further without significantly harming surrounding normal tissue. There is a further need to develop methods for introducing an exogenous chromophore into sebaceous glands where such chromophore would normally lack affinity for sebaceous gland material.

BRIEF SUMMARY OF THE INVENTION

Embodiments of the present invention are directed to methods in humans which are useful in treating skin conditions associated with the production or overproduction of sebum by sebaceous glands. Sebaceous glands are treated according to one method of the present invention in a manner to reduce or prevent the production of sebum without significantly harming or otherwise adversely affecting surrounding normal tissue. Methods of the present invention also include treating unwanted skin conditions associated with sebum production, such as acne. According to the present invention, the production of sebum is reduced in a manner to reduce, prevent or eliminate the occurrence or reoccurrence of unwanted skin conditions, such as acne.

According to one embodiment of the present invention, a chromophore, such as a dye, is administered to the site of irradiation. The term "chromophore" also includes compounds having chromophoric groups such as nitro groups, azo, alkylene units, esters, carbonyl groups, aldehydes, alkynes, aromatic rings, heterocyclics, carboxylic acids and the like. The chromophore acts to selectively absorb the chosen wavelength of laser light thereby enhancing the effectiveness of the irradiation. Other chromophores or photoactive or photoabsorbable compounds can be used which themselves act as therapeutic or cytotoxic agents upon irradiation. According to the methods of the present invention, an exogenous chromophore is selectively introduced into a holocrine gland, such as a sebaceous gland, selected for treatment. The exogenous chromophore preferably absorbs laser light having a wavelength significantly outside the wavelengths absorbed by skin or skin components. According to one embodiment, an otherwise lipophobic exogenous chromophore is rendered substantially lipophilic so as to be selectively introduced into sebaceous glands. The sebaceous glands having the chromophores introduced therein are then irradiated with laser light having a wavelength, duration, fluence and spot size selected to preferentially heat the sebaceous glands in a manner to disrupt, reduce, eliminate or otherwise interfere with the production of sebum. According to one embodiment, the sebaceous glands are heated to the point of denaturation and to effectively prevent the production of sebum that is required for the development or continued presence of unwanted skin conditions such as acne.

Other features and advantages of certain embodiments of the present invention will become more fully apparent from the following description taken in conjunction with the accompanying figures and claims.

BRIEF DESCRIPTION OF THE DRAWINGS

The patent file contains at least one drawing executed in color. Copies of the patent publication with color drawings will be provided by the U.S. Patent and Trademark Office upon request and payment of the necessary fee.

In the course of the detailed description of certain preferred embodiments to follow, reference will be made to the attached figures, in which.

FIG. 2 shows that indocyanine green is present in the sebaceous glands but not in the tissue between the glands.

DETAILED DESCRIPTION OF CERTAIN PREFERRED EMBODIMENTS

Figure 1:
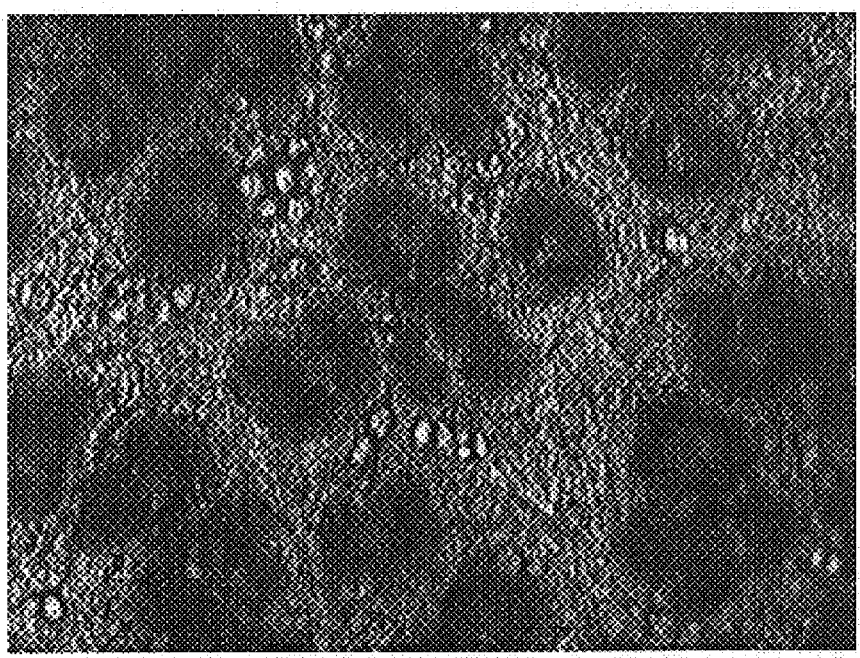
FIG. 1 is a photomicrograph showing tissue containing sebaceous glands viewed under normal illumination with white light wherein the tissue has been treated with a topical administration of indocyanine green which has been rendered lipophilic.

The principles of the present invention may be applied with particular advantage to treat unwanted skin conditions or disorders associated with the production or overproduction of sebum by sebaceous glands. According to the teachings of the present invention, sebaceous glands or other components of the pilosebaceous unit such as the infundibulum opening are altered, modified or disrupted by selectively introducing one or more exogenous agents, dyes or chromophores to the sebaceous glands in the affected area of skin to enhance the absorption of laser light at a site of irradiation within the skin and to also aid in the selective absorption of laser light. Exogenous chromophores or compounds including chromophoric groups are administered to take advantage of the deeper tissue penetration of longer visible or near-infrared wavelengths. One or more photoactivated compounds can also be administered as necessary to therapeutically treat the affected area of the skin. The amount, duration and mode of administration of the chromophore or other photoactive agent will depend on its properties and the makeup of the individual on which the treatment is to be carried out.

The affected area of skin is then irradiated with light having a wavelength strongly absorbed by the chromophore. The light has a wavelength, duration, fluence, and spot size sufficient to result in heating of the chromophore in the sebaceous glands such that the sebaceous glands are modified, altered, destroyed, damaged, disrupted or otherwise rendered incapable of producing sebum at excessive or normal levels. According to one embodiment, the sebaceous glands are prevented from producing sebum necessary to promote or sustain unwanted skin conditions such as acne. In other embodiments, the sebaceous glands may be disrupted to alleviate symptoms of medical conditions other than acne, e.g. seborrheic dermatitis commonly seen in infants and in HIV patients.

In one embodiment, the laser light is produced by a tunable pulsed dye laser system or diode laser system and is characterized as having a wavelength corresponding to that which is absorbed by the selected chromophore. Preferably, the laser light also has a wavelength that is substantially transmitted by the outer layers of the skin, i.e., the first 1 to 2 millimeters of skin. "Substantially transmitted" is used herein to indicate that not less than 60% of the laser light is transmitted through the first 2 millimeters of skin, or alternatively, not less than 60% of the laser light reaches target sebaceous glands. In general, suitable pulsed dye laser systems useful in the present invention include a power source, a flashlamp capable of emitting multiple pulses of light, a dye reservoir containing a dye suitable for stimulated emission of light, and an optical resonator having an output coupler. The power source, flashlamp, dye reservoir and optical resonator are operatively connected so as to generate multiple pulses of laser light having a defined wavelength and pulse duration. An optical fiber is optically coupled to the optical resonator in a manner to allow the multiple pulses of laser light to travel from the optical resonator through the optical fiber to the tissue area to be irradiated with a defined pulse fluence. A handpiece delivery system incorporating the terminal end of the optical fiber is used to effectively direct the laser light source to the target area.

In a second embodiment, light is produced by a tunable dye system that emits light continuously. That is, light is emitted continuously from the source. Preferably, the light has a wavelength that is substantially transmitted by the outer layers of skin. Suitable light system have a light source, such as an arc lamp, a dye reservoir for selecting the wavelength of light emitted from the system, a monochromator, and one or more shutters to prevent passage of the light. The shutter can be opened and closed using a pre-selected delay time to provide for pulsing of the light. For example, the shutter can be opened for about 1 ms and then closed for about 1 second to provide for a pulse duration of about 1 ms with a delay time of about 1 second. An optical fiber is optically coupled to the light system in a manner to allow the multiple pulses of light to travel from the optical resonator through the optical fiber to the tissue area to be irradiated with a defined pulse fluence. A handpiece delivery system incorporating the terminal end of the optical fiber is used to effectively direct the light source to the target area.

According to one embodiment, useful wavelengths are between about 700 nm and about 1200 nm, preferably between about 750 nm and about 850 nm and more preferably between about 800 nm and about 820 nm. 810 nm is a particularly preferable wavelength since melanin, the primary human skin pigment, does not absorb strongly at that wavelength. Additionally, commonly used topical acne treatments, such as Retin-A® (all-trans-retinoic acid), typically absorb light at about 351 nm. Thus, acne patients may undergo the treatment methods described here while continuing with other topical acne treatments. The laser light has a pulse duration less than the thermal relaxation time of the volume of tissue being irradiated. Specific pulse durations include between 0.1 msec and about 500 msec, preferably between about 1 msec and about 200 msec. The delivered fluence of the pulsed laser light is between about 1 J/cm$^2$ and about 50 J/cm$^2$, preferably between about 5 J/cm$^2$ and about 40 J/cm$^2$ and more preferably about 10 J/cm$^2$. The irradiated spot size is sufficient to include the manifestation of the unwanted skin condition of interest as a whole or portions thereof. According to an additional embodiment, the spot size is sufficient to include not only the acne, but also an area of normal tissue adjacent to or surrounding the acne to be treated which may include sebaceous glands which have not yet developed into visible acne, e.g. preferentially the entire holocrine gland and surrounding tissue including other sebaceous glands are treated. The area of visibly normal tissue adjacent to or surrounding the acne to be treated is referred to herein as the "margin" or "margin of tissue." Alternatively, the laser light has a spot size sufficient to irradiate only the margin or portions thereof, or part of the margin and part of the acne. Spot sizes in accordance with the present invention include those between about 1 mm to about 20 mm, preferably about 5 mm to about 15 mm. Depending upon the intended use and the size of the subject's sebaceous glands, the spot size may be smaller, e.g. about 500 μm to about 1 mm for use in infants, or larger, e.g. about 20 mm to about 30 mm for use in adults having larger sebaceous glands. In preferred embodiments, the spot size may be reduced during use by adjustment of the optical fiber aperture, e.g. the spot size can be increased or decreased during use.

According to the present invention, the area of the individual to be treated should be irradiated at least once with laser light having the above parameters, with the appropriate number of pulses necessary to treat the entire area. The complete treatment may be repeated up to five times with at least one week between each treatment.

It is to be understood that other lasers, such as yellow, green and blue wavelength lasers which produce laser light suitable of being absorbed by an exogenous chromophore taken up by or otherwise introduced into sebaceous glands, are useful within the scope of the present invention and include Argon ion lasers, Copper-vapor lasers, alexandrite lasers, ruby lasers, semiconductor diode lasers, frequency-doubled Nd:YAG lasers, and other dye lasers pumped by a Nitrogen laser or Argon-ion laser and the like. The lasers and other light sources within the scope of the present invention are preferably pulsed but may also operate in a continuous-wave (cw) mode with a scanner to automatically scan the treatment area and provide temporal modulation of the laser intensity on the treatment site.

The advantage of the selective photothermal sebaceous gland targeting over conventional methods of disrupting sebaceous gland activity include the more efficient use of laser light should a chromophore be used that absorbs at a wavelength substantially transmitted by skin or skin components. In addition, such a chromophore when rendered substantially lipophilic provides selective loading of the chromophore into the sebaceous glands versus surrounding tissue. This allows for a method of discriminating between sebaceous glands as opposed to surrounding tissue for purposes of absorption of laser light.

According to the invention, the sebaceous glands are irradiated to the extent to cause irreversible damage to the sebaceous glands but also in a manner to spare surrounding tissue, e.g. the thermal damage to surrounding tissue is minimal. This method is implemented, depending on the area of skin to be treated, by means of the pulsed dye laser or any other source of radiation preferentially absorbed by the exogenous chromophore selectively introduced into sebaceous glands.

According to additional embodiments, the methods described here may be used to treat skin conditions other than acne. For example, lipophilic chromophores may be administered or disposed on skin lesions. Because the rate of uptake of compounds by certain skin lesions may be larger than the rate of uptake in normal tissue, the skin lesions may be selectively destroyed using the methods described here. That is, the concentration of chromophores inside the skin lesion cells typically can be much larger than the concentration inside normal cellular tissue. Therefore, administration of light to the region of the skin lesions, destroys the skin lesions while minimizing the amount of normal tissue surrounding the skin lesions that is destroyed. Alternatively, the skin lesion can be injected with a chromophore prior to irradiation of the skin lesion.

The following examples are set forth as representative of the present invention. These examples are not to be construed as limiting the scope of the invention as these and other equivalent embodiments will become apparent in view of the present disclosure, figures and accompanying claims.

EXAMPLE I

Introduction of a Chromophore to Sebaceous Glands

The selective introduction of a chromophore to sebaceous glands is accomplished by topically applying a selected chromophore to the skin under conditions that permit the chromophore to selectively localize to the sebaceous glands. The selective introduction of a chromophore to sebaceous glands is most readily accomplished using lipophilic chromophores, or alternatively, by preparing less lipophilic chromophores in a carrier that renders them more lipophilic.

Chromophores useful in the methods of the invention should meet at least the following criteria. First, chromophores of use in the methods of the invention must strongly absorb light at a selected wavelength or portion of the spectrum. There are a large number of chromophores known in the art that meet this criterion, but particularly preferred among them are those that strongly absorb light energy at a wavelength or portion of the spectrum that is not strongly absorbed by natural skin pigments such as melanin, which absorbs at between about 500 nm to 600 nm.

A second criterion for a chromophore useful in the methods of the invention is that it be lipophilic, i.e., substantially soluble in a fat or lipid. The lipophilic nature of the chromophore facilitates the selective introduction of the chromophore to the sebaceous gland. Lipophilic chromophores include, for example, organic tissue stains and beta-carotene. Lipophilic chromophores may be dissolved in an acceptable oil and then applied directly to the area of skin one wishes to treat. Alternatively, the pores of the skin may be opened using heat, steam and the like to facilitate entry of the chomophores into the sebaceous glands.

It is recognized herein that a number of chromophores that absorb light energy at a wavelength or portion of the spectrum that is not absorbed by natural skin pigments, and thus might be expected to be useful for the methods of the invention, are not lipophilic. That is, there are a number of chromophores, particularly organic dye molecules, that would be useful in the methods of the invention except that they are not soluble in lipid or fat. Such chromophores include indocyanine green, methylene blue and other common dyes such as Rhodamine B and cresyl violet and the like. See also other chromophores useful in the present invention identified in U.S. Pat. No. 4,651,739, the disclosure of which is hereby incorporated by reference in its entirety for all purposes. The methods of the invention overcome this limitation by combining such chromophores with a lipophilic carrier preparation. In this way, the non-lipophilic chromophores are rendered lipophilic, allowing their selective introduction to the sebaceous gland.

Finally, a chromophore useful in the methods of the invention must be safe to apply to human skin. The chromophore must not be toxic or carcinogenic in the amounts to be applied. Data regarding toxicity and carcinogenicity of chemical compounds are widely known in the art.

EXAMPLE II

Rendering Non-Lipophilic Chromophores Lipophilic

According to one aspect of the present invention, non-lipophilic chromophores, for example, indocyanine green, are rendered lipophilic by several possible methods, including the use of liposomes and lipid suspensions. By associating a non-lipophilic chromophore with a lipid in either a liposome or a lipid suspension, the chromophore is selectively deposited within the sebaceous glands.

Liposomes containing a non-lipophilic chromophore are prepared using the following protocol. Appropriate amounts of the lipids are mixed in a beaker and melted at 75° C. The melt is then drawn into a syringe preheated in a water-bath at 75° C. A second syringe containing 0.05 M isotonic HEPES buffer, pH 7.4, is preheated to 70° C. The two syringes are then connected via a 3-way Teflon or metal stopcock. The aqueous buffer is then injected into the lipid phase syringe. The mixture is mixed back and forth between the two syringes rapidly several times while being cooled under cold tap water. This process is continued until the mixture is at room temperature. The resulting liposomal suspensions are then examined using a light microscope to assure integrity and quality of the liposomal preparations. A non-lipophilic chromophore may alternatively be prepared in a lipid suspension to facilitate selective introduction of the chromophore to sebaceous glands. Specifically, a chromophore may be placed in a lipid suspension by mixing an oil, a chromophore, which has been previously dissolved in a small amount (relative to the amount of oil) of water or alcohol, and one or more surfactants. Following vigorous stirring or shaking, the chromophore, dissolved in small water droplets, is suspended as an emulsion in the lipid. Following topical application, the suspended chromophore is then carried to the sebaceous glands due to its close association with the lipid.

The exact makeup of the lipid chromophore suspension may vary, and can include at least one pharmaceutically acceptable oil, at least one surfactant, and at least one chromophore dissolved in water or alcohol. Pharmaceutically acceptable oils for use in preparing lipid chromophore suspensions include, but are not limited to olive oil, sesame oil, corn oil, and safflower oil. Alternatively, the chromophore may be solubilized in one or more liquid vitamins, such as a tocopherol (Vitamin E), to provide for delivery of the chromophore and to promote epidermal health and maintenance.

As a general guideline, the ratio of oil to dissolved chromophore solution used to prepare a lipid chromophore suspension should be at least about 5:1, about 10:1, about 20:1, about 50:1, about 100:1, or even as high as 200:1 or more by volume. The chromophore is preferably, but not necessarily, dissolved in water or an alcohol acceptable for human topical administration at a concentration close to the limit of solubility for that chromophore. A preferred method of delivering ICG to the sebaceous gland would be a lotion with liposome-encapsulated ICG. The absorption and fluorescence characteristics of such lotion must be known to properly design the in vitro and in vivo experiments. A lipid suspension of ICG was prepared using the following protocol. 6 mg of ICG were dissolved in 20 g of water. 3 g of the solution were mixed with 9 g Tween 80, 15 g Span 80 and 23 g olive oil. The mixture was shaken for 1 min and left to settle for 3 days. The resulting solution is a uniform transparent liquid with negligible scattering. An identical clear lipid mix was prepared without dissolving ICG in water.

In this way, the concentration of the chromophore is kept as high as possible after mixing with surfactant and oil. Alcohols acceptable for topical administration include, but are not limited to ethanol, isopropanol and the like.

Surfactants useful in preparing lipid chromophore suspensions include, but are not limited to Tween 80 and Span 80. Generally, the surfactant comprises from 0.1% to 70% (w/v) of the lipid chromophore suspension. The amount may be varied depending primarily upon the amount and type of oil used and on the ratio of oil to dissolved chromophore solution used. Generally, the amount (mass or volume) of surfactant required varies in direct proportion to the volume of dissolved chromophore solution used; the greater the volume of chromophore dissolved in water or alcohol, the greater the proportion of surfactant necessary to maintain the lipid chromophore suspension.

The amount of chromophore added to a lipid chromophore suspension can vary from about 0.01% to about 25% by weight of the entire lipid chromophore suspension. The amount of chromophore used is determined empirically, using, for example, varied proportions of chromophore in lipid suspensions applied to the skin of an animal, followed by microscopic inspection to evaluate the density of chromophore localized in the sebaceous glands. Generally, the better a chromophore suspension localizes to sebaceous glands, the lower the relative proportion of chromophore necessary in the lipid chromophore suspension.

A specific lipid chromophore suspension was prepared as follows. 15 mg of ICG powder was dissolved in 1 g (1 ml) of water, followed by the addition of 3 g of Tween 80, 5 g of Span 80, and 7.667 g of olive oil. The suspension was vigorously shaken in a covered 50 ml tube for 5 minutes. The absorption coefficient for the resulting lipid chromophore suspension was measured and was typically between 350 $cm^{-1}$ and 690 $cm^{-1}$.

EXAMPLE III

Selective Introduction of a Chromophore to Sebaceous Glands

The manner in which a chromophore is selectively introduced to sebaceous glands depends upon whether the chromophore is lipophilic or non-lipophilic. A lipophilic chromophore is dissolved in a pharmaceutically acceptable oil and applied directly to the area of skin one wishes to treat. A lipophilic chromophore is dissolved in oil at a final concentration from about 0.001% to about 20% (w/v), with the proportion determined empirically using an animal model (e.g., the hamster ear model described herein or other appropriate model for human skin as known in the art).

A non-lipophilic chromophore is applied as chromophore-bearing liposomes or as a lipid ,chromophore suspension prepared as described herein. Following application of either a lipophilic chromophore in oil, chromophore-bearing liposomes or a lipid chromophore suspension, either by swabbing, for example with a cotton swab, a cotton ball or a paint brush, or by spraying or pouring the chromophore-oil mixture on the area to be treated, the mixture may be manually rubbed into the affected area to enhance the degree and/or rate of penetration of the mixture into the sebaceous glands. Generally, the mixture is contacted with the skin for about 2 minutes to about 24 hours prior to irradiation. The time of contact of the mixture and the concentration of chromophore applied is determined empirically using an animal model for a given chromophore preparation. The mixture may be applied to an entire area, for example, the face, or to a smaller portion of the area (e.g., a small portion of the face or back) one ultimately wishes to treat.

A chromophore is considered "selectively introduced" to sebaceous glands according to the invention if greater than or equal to about 90% of the chromophore remaining associated with the skin after removal of excess chromophore preparation from the skin surface is observed in sebaceous glands. The proportion of a particular chromophore localized to sebaceous glands from a particular chromophore preparation (e.g., chromophore in oil or chromophore in liposomes or lipid suspension) is determined using an appropriate animal model, such as the hamster ear model described herein. Hamsters are known to have sebaceous glands in their ears. These glands are typically on the order of 200 μm in diameter, making them somewhat larger than typical sebaceous glands in humans. Nonetheless, the hamster ear is a convenient and instructive model for human skin and sebaceous glands.

Figure 2:
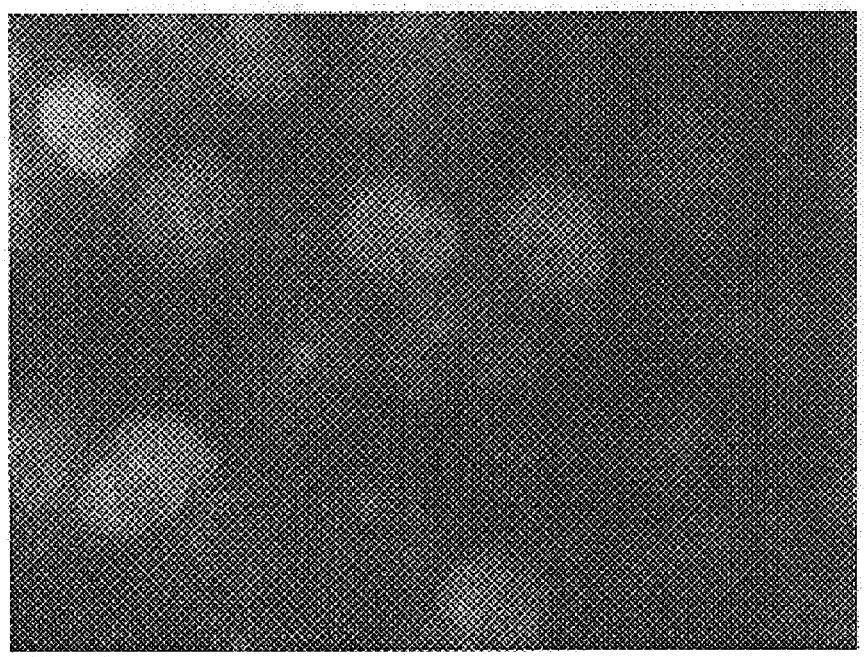
FIG. 2 is a photomicrograph of the same tissue shown in FIG. 1 but illuminated at 810 nm and observed through an 840 nm bandpass filter.

For example, the non-lipophilic chromophore indocyanine green was introduced to sebaceous glands present in skin of the hamster ear according to the following method. The lipid chromophore suspension was topically applied to hamster ears and allowed to travel into the pores and sebaceous glands for 24 hours. After this time, the hamsters were euthanized and their ears were examined for evidence of ICG in the sebaceous glands. FIG. 1 shows a photomicrograph of skin from a hamster ear treated with ICG, illuminated under white light, and FIG. 2 shows the same region illuminated under 810 nm light and observed through an 840 nm bandpass filter. ICG fluorescence (840 nm) is stimulated by irradiation with 810 nm light. Both the white light and fluorescence micrographs of the treated region show the chromophore is primarily localized to the sebaceous glands. Experimentally, it is estimated that approximately 5% of sebaceous gland lipid is ICG lipid.

Another method for evaluation of the ICG uptake is based on the use of Sebutape® adhesive patches commercially available from CuDerm Corp. (Dallas, Tex.). The patch consists of a microporous film acting as a passive collector of sebum. After the application of the ICG microemulsion and cleaning of the skin, a Sebutape® patch will be applied to the skin and analyzed for fluorescence. The lipid ICG microemulsion, if present on the skin surface, would penetrate into the patch and the patch would fluoresce under illumination with 810 nm light. The skin will be cleaned and a new patch will be applied until there is no fluorescence from the patch, thus indicating that the skin surface is clean from ICG. A fresh patch will be applied to the clean skin surface and kept there for an hour. After an hour on the skin, that patch will be examined for sebum collection and fluorescence. If the patch were applied to a skin site without active sebaceous glands there would be no sebum collected in the patch and thus no fluorescence. If the patch collects sebum, but there is no fluorescence, the ICG microemulsion did not penetrate in the sebum contained in the sebaceous gland. Such result would indicate that the application procedure for the ICG microemulsion has to be improved, e.g. it has to be applied for a longer time. If the patch collects sebum and there is fluorescence, the sebaceous glands are successfully loaded with ICG and they can be treated with the laser. The intensity of the fluorescence signal can be related to the ICG concentration in the sebum and the treatment fluence can be adjusted accordingly.

Another method for evaluation of the ICG uptake is with an appropriate imaging system. This imaging system will incorporate a monochrome CCD camera with a removable band-pass filter designed to selectively detect the ICG fluorescence. It will also incorporate various objectives to allow either large field, low resolution imaging or narrow field, higher resolution imaging. The camera will be connected to a frame grabber in a computer in order to digitally record the images and perform image treatment. It would be possible to identify the ICG loaded sebaceous glands and hair follicles on the fluorescence image. In addition, it is possible that the fluorescence image would reveal a residual layer of ICG microemulsion on the skin surface. Such layer would have a deteriorating effect on the penetration ability of the laser during the treatment and would contribute to unnecessary heating of the epidermis. The presence of such residual layer would indicate that the skin cleaning procedure would have to be repeated. The intensity of the fluorescence signal from the sebaceous glands can be related to the ICG concentration in the sebum and the treatment fluence can be adjusted accordingly.

Figure 3:
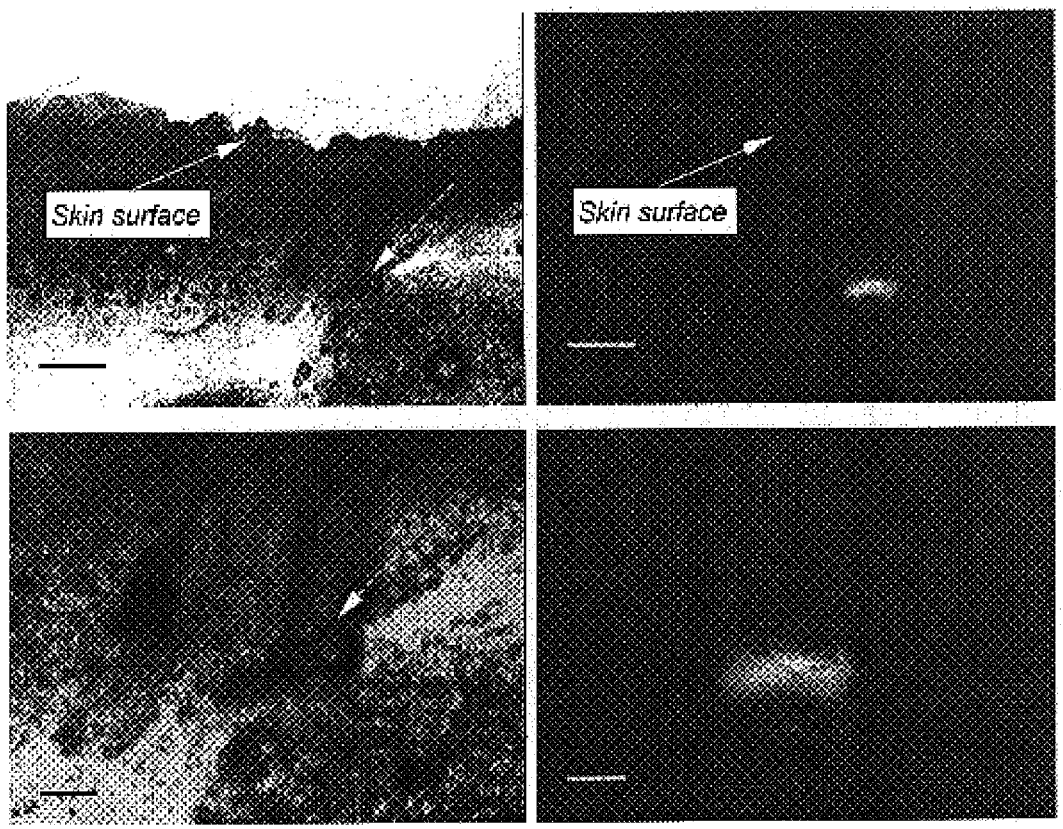
FIG. 3 is a sample of human skin treated with an indocyanine green microemulsion for 24 hours before excision.

Selective delivery of ICG in the sebaceous glands in human skin using a biopsy sample was performed. For this study, an eligible patient was scheduled to have some undesirable skin lesions surgically excised. The day before the surgery, an ICG-containing lipid solution was applied to the margin area of the skin that is normally excised around the skin lesion. After the surgical excision of the lesion and the margin area, the margin area was sent for fluorescence analysis. The samples of excised marginal skin were sectioned as thin slices and mounted on microscope slides. FIG. 3 shows the images obtained from such sample with normal light (left panels) and with a fluorescence band-pass filter under illumination with the 810 nm diode laser (right panels). The dashed arrow points to a pilosebaceous unit with attached sebaceous gland.

The fluorescence photographs confirm the selective delivery of the ICG microemulsion to the sebaceous glands in the human skin. The absence of fluorescence at the skin surface means that the excess ICG microemulsion was removed from the skin surface and thus there is no risk of injuring the epidermis with heat generated in a residual ICG film.

EXAMPLE IV

Methods of Clearing Obstructed Pores Prior to Chromophore Administration

According to an additional embodiment of the present invention, the surface of the skin to be treated with the chromophore is cleaned prior to chromophore administration to remove any excess surface oils and debris which could potentially block the lipophilic absorption of the chromophore into the targeted sebaceous glands. When subjected to the cleaning step, pores which may be either partially or wholly obstructed by buildup of sebum, oil, dirt, cosmetics or other foreign material are partially or wholly cleared to allow or otherwise improve access of the chromophore to the sebaceous gland. In this manner, delivery of the chromophore to the targeted sebaceous gland is enhanced when compared to administrations of chromophores where the skin a has not been cleaned and the pores have not been cleared.

According to this aspect of the present invention, a 10 cm×10 cm area of skin to be treated was wiped with an alcohol swab. A 70% glycolic acid solution was then applied to the skin surface and then left on for about 5 minutes. The glycolic acid solution was then neutralized with GLYTONE® post peel neutralizer available from Genesis Pharmaceutical Inc. (Morristown, N.J.), and the area was dried. Other suitable neutralizing agents include but are not limited to water, sodium bicarbonate solutions, e.g. 5% sodium bicarbonate, etc. The neutralization process was performed by wiping the area with water, e.g. using a water-soaked gauze pad, and subsequently applying a liberal amount of the neutralizer on the treated skin area. The treated area was then rinsed liberally with water. A lipophilic formulation of indocyanine green was then topically applied to the skin area and covered with an occlusive dressing for 24 hours.

Additional methods for removing excess surface oils and debris from skin and for clearing pores include topical administration of salicylic acid preparations in the forms of washes, gels or peels; topical retinoic acid therapy; and mechanical processes including microdermabrasion. The area of the skin to be cleaned may optionally be heated to promote pore opening and to facilitate better cleaning of the skin area. It is to be understood that additional methods for clearing pores which are useful in the present invention will become apparent to those skilled in the art based upon the present disclosure.

EXAMPLE V

Irradiation of Sebaceous Glands Containing Selectively Introduced Chromophore

Irradiation of an area of skin being treated by a method of the present invention is accomplished with a laser that emits light energy at a wavelength strongly absorbed by the selected chromophore, but largely transmitted by the outer layers (first 1–2 mm) of the skin. For example, a preferred chromophore, indocyanine green (ICG; also known as cardio green) absorbs strongly at 810 nm, a wavelength at which melanin, the primary human skin pigment, does not absorb strongly. Thus, a laser emitting light at this wavelength is preferred if ICG is used as the chromophore.

The laser radiant energy, or fluence of laser light useful according to the invention will vary with the absorption coefficient of the chromophore used and may be predicted by a Monte Carlo simulation of the laser-tissue interaction, or may be determined empirically using an appropriate animal model. In a Monte-Carlo computer simulation, the occurrence of each of the possible mechanisms for interaction between the laser radiation and the target tissue is assigned a probability. The path of a single quantum of laser radiation through the target tissue is then divided into many small steps. At each step, the overall effect of the radiation is determined by chance consistent with the assigned probabilities. This process is repeated many times until a statistically valid picture of the overall effect is obtained. In a typical application, experimental data are used to determine the probability assignments. There is a number of Monte-Carlo simulation packages that are commercially available. The Monte-Carlo simulation package used here is derived from the work of L. H. Wang, S. L. Jacques, and L. Q. Zheng, "MCML—Monte Carlo Modeling of Photon Transport in Multi-layered Tissues", Computer Methods and Programs in Biomedicine 47, 131–146 (1995) and L. H. Wang, S. L. Jacques, and L. Q. Zheng, "CONV—Convolution for Response to a Finite Diameter Photon Beam Incident on Multi-layered Tissues", Computer Methods and Programs in Biomedicine 54, 141–150 (1997) and is available through the Internet.

The fluence is directly related to laser intensity, and should be maintained as low as possible to effect thermal disruption of sebaceous glands that have concentrated the chromophore while limiting damage to surrounding tissues. Optimal fluences range from about 0.1 $J/cm^2$ to about 50 $J/cm^2$. For indocyanine green, for example, it is preferred that the fluence of the light emitted by the laser is in the range of about 5 $J/cm^2$ to about 40 $J/cm^2$.

It is preferred that the laser be pulsed during the irradiation of the area being treated. Pulse duration may vary over a range of approximately 1 μsec to approximately 500 msec, depending upon the laser used, the chromophore used, and the amount of chromophore selectively introduced to the sebaceous glands. Longer pulses are generally more effective for disruption of larger glands that have longer thermal relaxation times than are short pulses. When using indocyanine green as the chromophore, for example, the pulse duration should be about 1 to about 100 msec.

The pulse duration and fluence determine the laser intensity delivered to the treated area. The intensity should be low enough to minimize the formation of a shockwave that can damage surrounding tissue and to minimize tissue vaporization or explosive tissue ablation.

According to the present invention, the amount of ICG that must be introduced and the fluence required to damage the sebaceous gland is estimated based upon the estimated temperature rise in the gland at a given fluence and pulse duration. A temperature rise of 30° C. sustained for more than about 10 msec is sufficient to disrupt the gland. Tables I and II show the results of such estimates obtained by means of a Monte Carlo simulation of the laser:tissue interaction. For this estimate, the gland is assumed to have 5% ICG lipid. The results depend strongly upon the absorption coefficient of ICG in the lipid chromophore suspension. Experimentally, this coefficient was found to lie between the limits given in the tables (i.e., 350 $cm^{-1}$ to 690 $cm^{-1}$).

The expected temperature rise ($\Delta T$) of a gland for the case in which fluence incident in the tissue is 10 $J/cm^2$ and the pulse duration is either 50 or 20 msec are shown in Tables I and Table II respectively.

TABLE I

Calculated Temperature Rise Expected
within the Sebaceous Gland in ° C.
Pulse Duration 50 ms, 10 $J/cm^2$ on the skin surface in a 5 mm spot (39W)

| Lipid ICG | Gland Diameter | | |
|---|---|---|---|
| | 50 μm | 100 μm | 200 μm |
| 5% 350 $cm^{-1}$ | 3 | 10 | 30 |
| 5% 690 $cm^{-1}$ | 6 | 19 | 55 |

TABLE II

Calculated Temperature Rise Expected
in the Sebaceous Gland in ° C.
Pulse Duration 20 ms, 10 $J/cm^2$ on the skin surface in a 5 mm spot (98W)

| Lipid ICG | Gland Diameter | | |
|---|---|---|---|
| | 50 μm | 100 μm | 200 μm |
| 5% 350 $cm^{-1}$ | 5 | 19 | 49 |
| 5% 690 $cm^{-1}$ | 10 | 35 | 89 |

The size of the gland has an effect on the expected temperature rise, as seen in the table, with a nearly 10-fold increase in expected $\Delta T$ in 200 μm glands compared to 50 μm glands at either fluence or pulse duration setting. It is evident from the table that at 1% lipid solution uptake, and if the absorption coefficient of the lipid chromophore solution is actually closer to the lower limit given, that one would need to increase the fluence above 10 $J/cm^2$ to achieve disruption of the gland. On the other hand, at the upper limits of both the absorption coefficient and lipid chromophore uptake, 10 $J/cm^2$ suffices to achieve disruption. With a lower pulse, 10 $J/cm^2$ may be sufficient to achieve disruption in the larger glands.

Since one experimentally finds approximately 5% of the gland volume is filled with lipid chromophore solution, the range of 5 $J/cm^2$ to 40 $J/cm^2$ for fluence and 1 msec to 100 msec for fluence will allow the practitioner to achieve disruption of a broad range of gland sizes.

Laser energy may be transmitted to the area being treated by, for example, a commercially available optical fiber. One end of the fiber is affixed to a laser light source, such as a diode laser that emits light in a wavelength strongly absorbed by the selected chromophore, and the other end is directed towards the area to be irradiated. The size of the optical fiber aperture, e.g. the diameter of the spot emitted by the optical fiber, is selected based upon the size of the area to be treated, with smaller fibers suited to smaller areas and larger fibers suited to larger areas. The laser itself is connected to a control panel to enable the user to turn the laser on and off and to adjust the fluence and pulse rate of the laser energy.

The laser energy may be applied by scanning the emitting end of the optical fiber over the area being treated. Scanning is accomplished by manually moving the optical fiber or the laser itself over the area being treated. Alternatively, it is contemplated that the scanning may be accomplished mechanically by mounting the laser or the emitting end of the optical fiber on a scanning apparatus designed to move at a controlled rate. In this manner the total laser energy applied to any one given area may be kept constant. Clearly, this latter approach is most useful when relatively large areas are to be treated.

While any laser that emits light energy at a wavelength and intensity sufficient to disrupt the function of sebaceous glands that have had a chromophore selectively introduced is acceptable for use in the methods of the invention, a preferred embodiment employs a diode laser and indocyanine green as the chromophore. It is preferred that the diode laser have a wavelength range of 750 nm to 1100 nm, a pulse duration ranging from about 1 to about 100 msec, and a fluence range of about 5 $J/cm^2$ to about 40 $J/cm^2$.

Figure 4A:
FIGS. 4A and 4B are histological studies from a human volunteer with active acne.
Figure 4B:
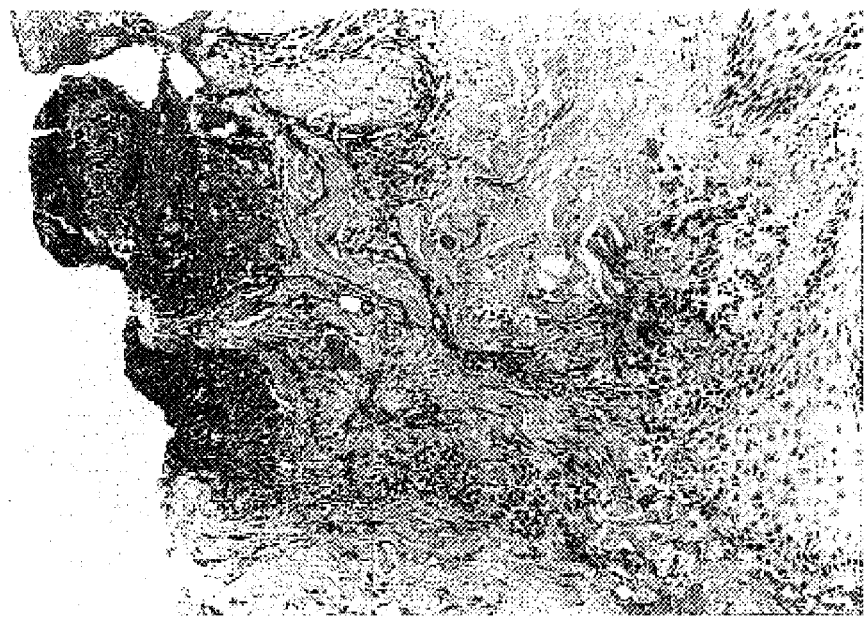

A human volunteer with active acne on the back had a small area treated with the ICG microemulsion and the laser. Twenty-four hours after the treatment a punch biopsy sample was taken from the treated area and it was processed for histological examination. FIGS. 4A and 4B show the results of a histological examination. The low power view (FIG. 4A) and the high power view (FIG. 4B) both show that the folliculosebaceous units have largely been destroyed with surrounding tissue necrosis. Without wishing to be bound by an scientific theory, a pathology analys revealed that the folliculosebaceous unit at the far left of FIG. 4A had largely been destroyed with surrounding tissue necrosis. The pathology analysis further revealed that the folliculosebaceous unit in the middle of the field in FIG. 4A also was largely destroyed with acute inflammation and necrosis involving the follicular epithelium. Without wishing to be bound by an scientific theory, a pathology analysis under high power (FIG. 4B) revealed that the left folliculosebaceous unit had a destroyed follicle and the middle folliculosebaceous unit had acute inflammatory cells present within follicular epithelium in the middle.

EXAMPLE VI

The effectiveness of treatment in reducing sebum production is determined by direct measurement of sebum production following the laser irradiation. Sebum production is measured, for example, using a specialized sebum-absorbent tape, SEBU-TAPES™ (CuDerm Corp., Dallas, Tex.) and image analysis techniques. SEBU-TAPES™ are white, open celled, microporous, hydrophobic films coated with an adhesive layer that adheres to the skin surface. As sebum is secreted, it is absorbed by the tape, displacing air in the microcavities. As the microcavities in the tape fill with sebum, the lipid-filled cavities become transparent. The area covered by transparent spots per $cm^2$ is a convenient and reproducible measure of sebum production (Manuskiatti et al., 1999, J. Amer. Acad. Dermatol. 41: 176–180). In order to observe a change in sebum production following treatment with the methods of the invention, one may either measure a treated area and an untreated nearby area on the same individual, or one may measure sebum production over a standard amount of time (e.g., 10 min to 10 hrs) on the area to be treated both before and after treatment. Sebum production is considered "reduced" according to the invention if it is at least 20%, preferably at least 40%, more preferably at least 50%, 60%, 70%, 80% or even greater than or equal to 90% lower relative to sebum production either by untreated skin in a similar location or by the treated area prior to treatment.

An alternative method of measuring sebum production is to examine hematoxylin and eosin-stained sections of punch biopsy tissue from treated and untreated areas of the same individual, taking note of the size and morphology of the sebaceous glands before and after treatment. Altered morphology of sebaceous glands is generally indicative of successful treatment, since altered gland morphology is associated with reduced sebum production.

The reduction of sebum production accomplished through the inventive method results in a reduction in the presence and/or severity of acne. The presence or severity of acne may be quantified according to the method of Michaelsson et al. (1977, Arch. Determatol. 113: 31–36). Briefly, the number of comedones, papules, pustules and infiltrates in an area to be treated are recorded. Each type of lesion is given a severity index: 0.5 for comedones, 1 for papules, 2 for pustules and 3 for infiltrates. A total score that corresponds to the severity of the disease is obtained by multiplying the number of each type of lesion with its severity index and calculating the sum of the various lesions (Sigurdsson et al., 1996, Dermatology 194: 256–260). A decrease in the acne severity score of at least 10% or more, preferably 25% or more, 50% or more, 75% or more up to and including a decrease to the score of zero (i.e., no acne), is indicative of reduced acne severity or presence according to the invention.

Figure 5A:
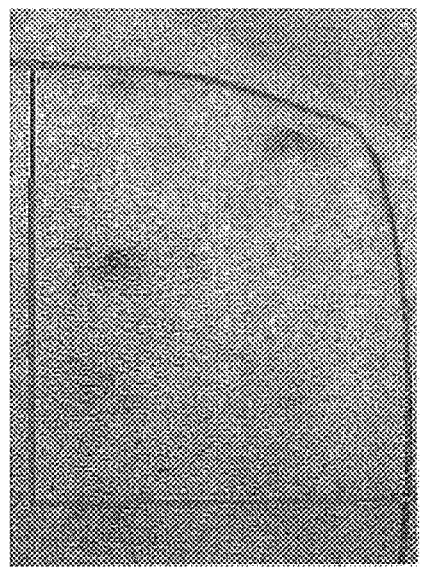
FIGS. 5A–5D are photographs showing a reduction in acne after treatment using the invention described here.
Figure 5B:
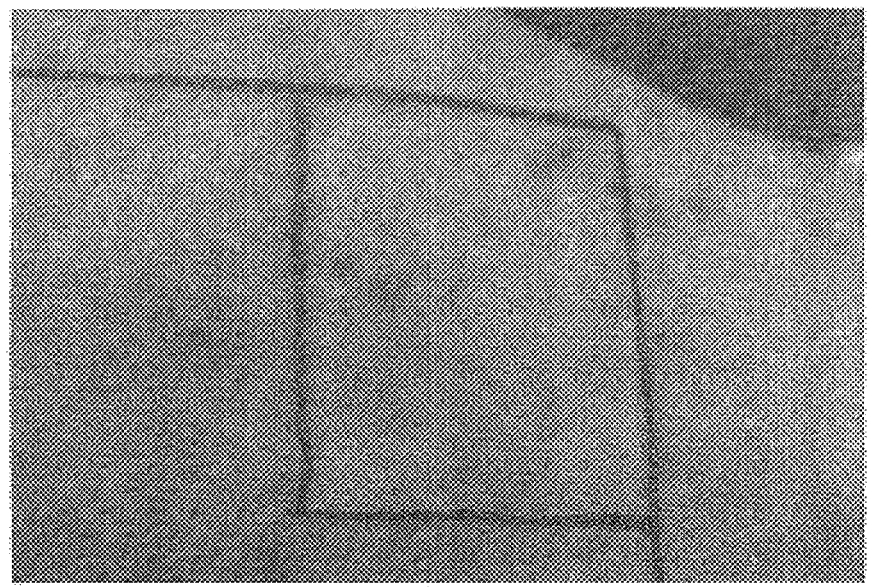
Figure 5C:
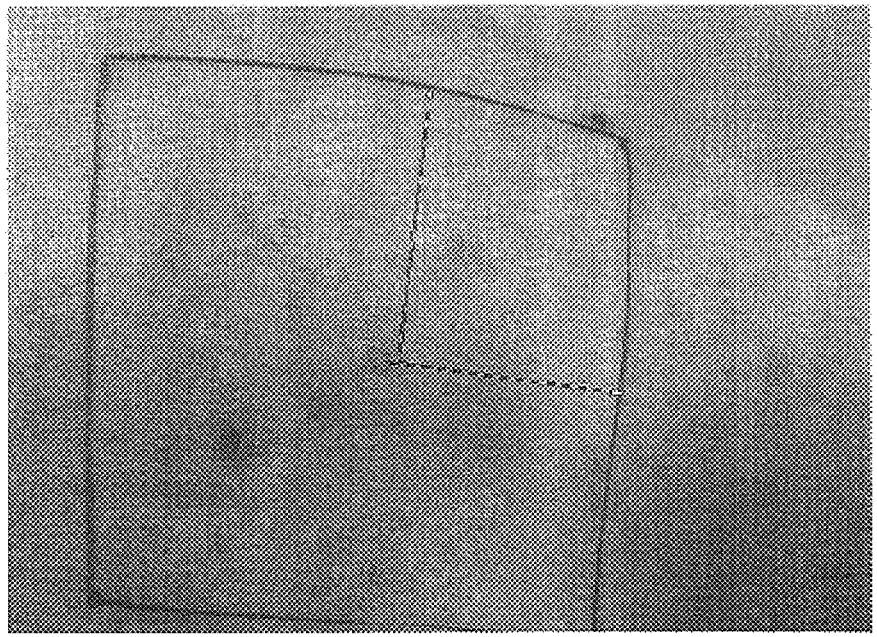
Figure 5D:
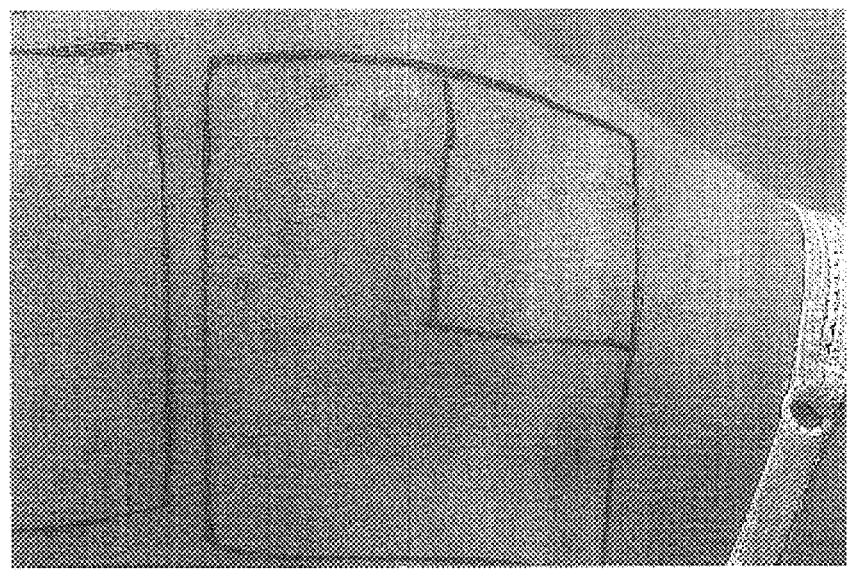

EXAMPLE VII 10 treatment sites were chosen on the backs of patients with active acne. Topical indocyanine green dye in a lipophilic carrier was then applied to a 10 cm×10 cm area treatment site and covered with an occlusive dressing for 24 hours. The area was then cleaned with alcohol and treated with laser irradiation with a laser from Cynosure, Inc. (Chelmsford, Mass.). The following laser parameters were used: wavelength of 800 nm, 4 mm spot size, 50 msec pulse duration with a pulse fluence of 40 $J/cm^2$. Photographs of the treatment area were taken prior to the laser irradiation (FIG. 5A) as well as 10 days (FIG. 5B), 10 weeks (FIG. 5C), and 10 months (FIG. 5D) post irradiation. The photographs taken 10 days, 10 weeks, and 10 months post treatment showed a significant reduction in the presence of visible acne (see rectangular regions in FIGS. 5B, 5C and 5D).

In addition to the treatment of existing acne, the invention also provides a way to prevent the development of acne. The method essentially comprises the steps of selectively introducing a chromophore to sebaceous glands, and then irradiating the sebaceous glands and surrounding area with laser light of a wavelength that is essentially transmitted by the outer layers of human skin and is strongly absorbed by the chromophore. The irradiation is performed at a light fluence and for a time sufficient to disrupt sebaceous gland function such that the development of acne is prevented.

It is to be understood that the embodiments of the present invention which have been described are merely illustrative of some of the applications of the principles of the invention. Numerous modifications may be made by those skilled in the art based upon the teachings presented herein without departing from the true spirit and scope of the invention.

What is claimed is:

1. A method of treating a patient who has an unwanted skin condition associated with the production of sebum, the method comprising:

generating, on the patient's skin, a target region having substantially clear pores, wherein generating the target region comprises applying an acidic composition to an area of the patient's skin and heating or mechanically abrading the area;

topically administering an exogenous chromophore onto the target region, wherein the chromophore absorbs laser light having a wavelength between about 700 nm to about 1200 nm; and irradiating the target region with laser light having a wavelength between about 700 nm to about 1200 nm form a time sufficient to inhibit subsequent sebum production within the target region.

2. The method of claim 1, wherein applying an acidic composition to an area of the patient's skin comprises topically applying a glycolic acid solution or a salicylic acid preparation to the area.

3. The method of claim 2, wherein the acidic solution is a glycolic acid solution and the method further comprises the step of neutralizing the glycolic acid solution by administering at least one neutralizing agent to the target region.

4. The method of claim 3, wherein the neutralizing agent is water, a sodium bicarbonate solution, or GLYTONE®.

5. The method of claim 1, wherein the glycolic acid solution is a 70% glycolic acid solution.

6. The method of claim 1, further comprising, prior to the step of generating the target region, a step of wiping an area of the patient's skin with alcohol, wherein the area subjected to wiping is substantially the same as the target region.

7. The method of claim 1, wherein the unwanted skin condition is acne.

8. The method of claim 1, wherein the chromophore is a lipophilic chromophore.

9. The method of claim 8, wherein the lipophilic chromophore is beta-carotene.

10. The method of claim 1, wherein the chromophore is a dye.

11. The method of claim 10, wherein the dye is indocyanine green, Rhodamine B, or cresyl violet.

12. The method of claim 1, wherein the chromophore is combined with a lipophilic carrier.

13. The method of claim 12, wherein the lipophilic carrier is a liposome.

14. The method of claim 12, wherein the lipophilic carrier is a lipid suspension.

15. The method of claim 14, wherein the lipid suspension comprises an oil or a surfactant.

16. The method of claim 15, wherein the oil is a sunflower oil, an olive oil, or a safflower oil.

17. The method of claim 1, wherein the wavelength is between about 750 nm and about 850 nm.

18. The method of claim 1, wherein the wavelength is between about 800 nm and about 820 nm.

19. The method of claim 1, wherein irradiating the target region with laser light comprises irradiating the target region with laser light having a pulse duration of about 200 msec.

20. The method of claim 1, wherein irradiating the target region with laser light comprises irradiating the target region with laser light having a pulse duration of about 500 msec.

* * * * *